US00PP25312P2

(12) United States Plant Patent
Heuger

(10) Patent No.: US PP25,312 P2
(45) Date of Patent: Feb. 24, 2015

(54) *HELLEBORUS* PLANT NAMED 'COSEH 1070'

(50) Latin Name: *Helleborus niger*
Varietal Denomination: COSEH 1070

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 126 days.

(21) Appl. No.: 13/815,557

(22) Filed: Mar. 8, 2013

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 1070', characterized by its upright and mounding plant habit; uniform and freely flowering habit; dark green-colored leaves with yellow green and greyed green-colored marbling; freely flowering habit; single white-colored flowers; and good garden performance.

2 Drawing Sheets

Botanical designation: *Helleborus niger.*
Cultivar denomination: 'COSEH 1070'.

BACKGROUND OF THE INVENTION

The present invention relates to a new and distinct cultivar of *Helleborus* plant, botanically known as *Helleborus niger* and hereinafter referred to by the name 'COSEH 1070'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in January, 2006 of two unnamed proprietary seedling selections of *Helleborus niger*, not patented. The new *Helleborus* plant was discovered and selected by the Inventor as a single flowering plant from within the progeny of the stated cross-pollination grown in a controlled greenhouse environment in Glandorf, Germany in December, 2008.

Asexual reproduction of the new *Helleborus* plant by divisions in a controlled greenhouse environment in Glandorf, Germany since March, 2009 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 1070'. These characteristics in combination distinguish 'COSEH 1070' as a new and distinct *Helleborus* plant:

1. Upright and mounding plant habit.
2. Uniform and freely flowering habit.

3. Dark green-colored leaves with yellow green and greyed green-colored marbling.
4. Freely flowering habit.
5. Single white-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger* 'HGC Josef Lemper', disclosed in U.S. Plant Pat. No. 15,615. In side-by-side comparisons conducted in Glandorf, Germany, plants of the new *Helleborus* differed primarily from plants of 'HGC Josef Lemper' in the following characteristics:

1. Plants of the new *Helleborus* had variegated leaves whereas plants of 'HGC Josef Lemper' had solid green-colored leaves.
2. Plants of the new *Helleborus* had smaller flowers than plants of 'HGC Josef Lemper'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 1070' grown in a container.

The photograph on the second sheet is a close-up view of a typical flower of 'COSEH 1070'.

DETAILED BOTANICAL DESCRIPTION

The aforementioned photographs and following observations, measurements and values describe plants grown during the late autumn in 13-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger* 'COSEH 1070'.

Parentage:

*Female, or seed, parent*.—Unnamed proprietary seedling selection of *Helleborus niger*, not patented.

*Male, or pollen, parent*.—Unnamed proprietary seedling selection of *Helleborus niger*, not patented.

Propagation:

*Type*.—By tissue culture.

*Time to initiate roots, winter*.—About two months at temperatures about 12° C.

*Time to produce a rooted young plant, winter*.—About six months at temperatures about 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held just above the foliar plane; plant shape is roughly globular; low vigor to moderately vigorous growth habit.

*Plant height*.—About 26.8 cm.

*Plant diameter* (*area of spread*).—About 27.4 cm.

Foliage description:

*Arrangement*.—Leaves arranged in a basal rosette; leaves palmately compound with five to seven leaflets per leaf.

*Leaf length*.—About 18.1 cm.

*Leaf width*.—About 11.3 cm.

*Leaflet length*.—About 6.4 cm.

*Leaflet width*.—About 2.5 cm.

*Leaf shape*.—Palmate; orbicular to reniform in outline.

*Leaflet shape*.—Obovate to narrowly obovate.

*Leaflet apex*.—Acute.

*Leaflet base*.—Attenuate.

*Leaflet margin*.—Serrate.

*Leaflet texture, upper and lower surfaces*.—Smooth, glabrous; leathery.

*Leaflet venation pattern*.—Pinnate.

*Leaflet color*.—Developing leaves, upper surface: Close to between 143C and 144A; marbling, close to 145A. Developing leaves, lower surface: Close to 138B. Fully developed leaves, upper surface: Close to between 137A and N137C; marbling, close to 144C and 192B; venation, close to 144A to 144B. Fully developed leaves, lower surface: Close to 191A to 191B; marbling, close to 147C to 147D; venation, close to 147D.

*Petioles*.—Length: About 9 cm. Diameter: About 5 mm. Texture, upper and lower surfaces: Smooth, glabrous. Color, upper and lower surfaces: Close to between 145C and 146D, heavily tinged with close to 184A to 184B.

Flower description:

*Flower shape and habit*.—Single rotate flowers arranged singly or in pairs; freely and uniform flowering habit with about 24 flowers and flower buds developing per plant; flowers facing mostly outwardly.

*Fragrance*.—None detected.

*Natural flowering season*.—Plants begin flowering about ten months after planting; plants flower from winter into the early spring in Germany.

*Flower longevity on the plant*.—About ten days; flowers not persistent.

*Flower buds*.—Length: About 1.9 cm. Diameter: About 1 cm. Shape: Ovate. Color: Close to 145B to 145C; towards the apex, close to 145D.

*Flower diameter*.—About 7.7 cm.

*Flower depth* (*height*).—About 2.1 cm.

*Petals*.—Transformed into nectaries.

*Sepals*.—Quantity and arrangement: Five, arranged in a single whorl. Length: About 3.9 cm. Width: About 2.4 cm. Shape: Ovate to obovate. Apex: Obtuse to bluntly acute. Base: Broadly cuneate. Margin: Entire. Texture, upper and lower surfaces: Smooth, glabrous. Color: When opening, upper surface: Close to NN155C; towards the base, close to 145B. When opening, lower surface: Close to NN155B; towards the base, close to 145B. Fully opened, upper and lower surfaces: Close to 155A; towards the base, close to 145A; color becoming closer to 145B to 145C development.

*Peduncles*.—Length: About 21.4 cm. Diameter: About 4 mm. Aspect: About 20° from vertical. Strength: Moderately strong. Texture: Smooth, glabrous. Color: Close to 146D, heavily dotted with close to 184A to 184B.

*Pedicels*.—Length: About 7.8 cm. Diameter: About 3 mm. Aspect: About 30° from peduncle axis. Strength: Moderately strong. Texture: Smooth, glabrous. Color: Close to 147D, moderately dotted with close to 184B.

*Reproductive organs*.—Stamens: Quantity per flower: About 100. Filament length: About 1.2 cm. Filament color: Close to NN155D. Anther shape: Reniform. Anther length: About 2 mm. Anther color: Close to 1B to 1C. Pollen amount: Moderate. Pollen color: Close to 5D. Pistils: Quantity per flower: About seven. Pistil length: About 8 mm. Stigma shape: Club-shaped. Stigma color: Close to 150D. Style length: About 7.5 mm. Style color: Close to 145A to 145B. Ovary color: Close to 145A to 145B. Nectaries (transformed petals): Quantity per flower: About ten. Length: About 1.2 cm. Diameter: About 4 mm. Shape: Obovate, concave. Color, immature, inner and outer surfaces: Close to 144A. Color, mature, inner and outer surfaces: Close to 144A; towards the apex, close to 144B to 144C; with development, apical color becomes closer to N144A.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 1070' as illustrated and described.

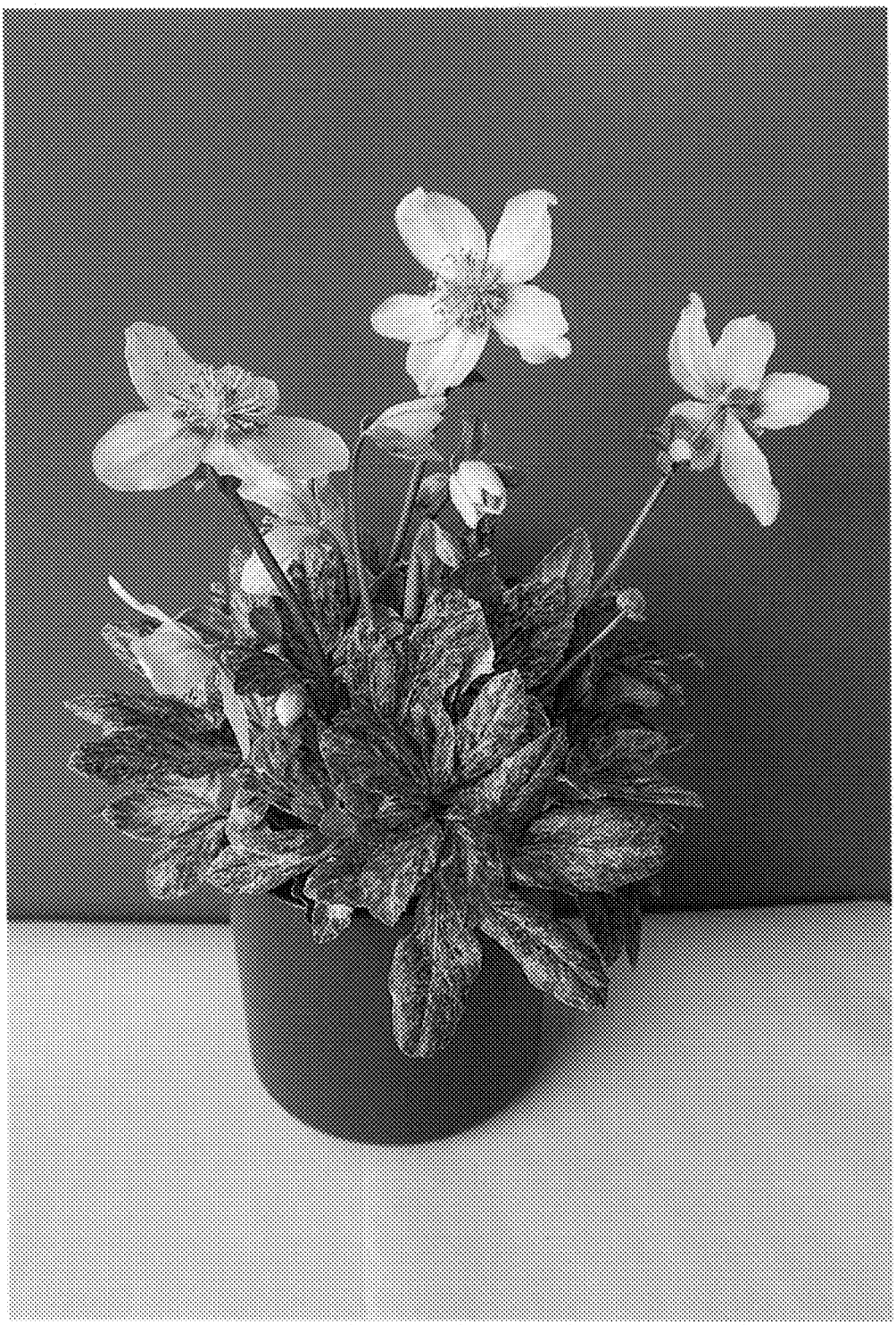

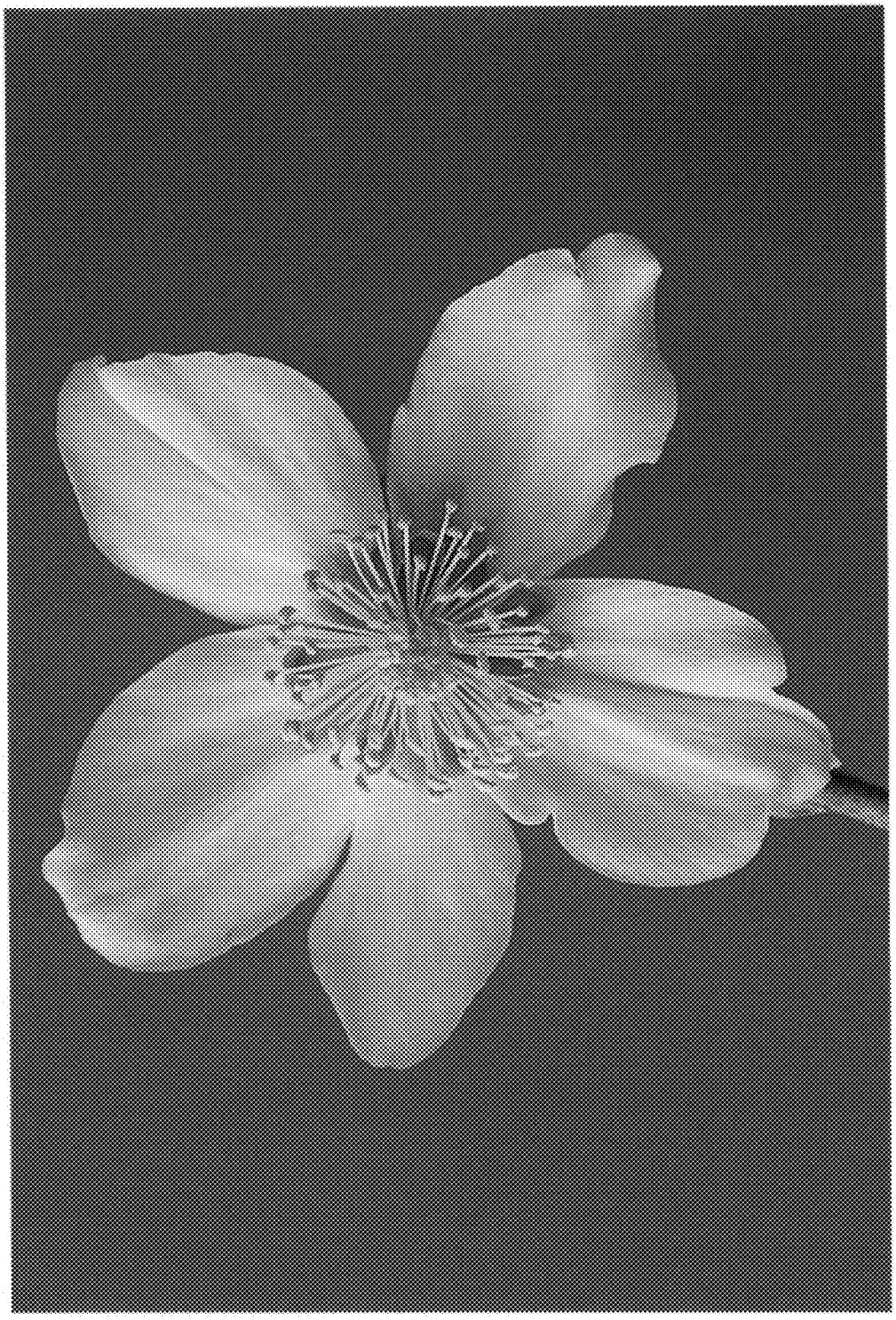

* * * * *